United States Patent
Baynham

(10) Patent No.: US 7,188,554 B2
(45) Date of Patent: Mar. 13, 2007

(54) MEDICAL FASTENER AND TOOL

(75) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 29 days.

(21) Appl. No.: 11/149,704

(22) Filed: Jun. 9, 2005

(65) Prior Publication Data
US 2006/0278049 A1    Dec. 14, 2006

(51) Int. Cl.
*B25B 23/00* (2006.01)
*F16B 23/00* (2006.01)
*B25B 13/48* (2006.01)

(52) U.S. Cl. .......................... 81/436; 411/402; 411/404
(58) Field of Classification Search .................. 81/436, 81/460, 176.2; 411/402–405, 410
See application file for complete search history.

(56) References Cited

U.S. PATENT DOCUMENTS

| | | | |
|---|---|---|---|
| 2,066,484 A * | 1/1937 | Phillips ....................... 411/404 |
| 2,083,092 A | 6/1937 | Richer | |
| 2,248,695 A * | 7/1941 | Bradshaw ................... 411/410 |
| 2,969,250 A | 1/1961 | Kull | |
| 3,584,667 A | 6/1971 | Reiland | |
| 3,874,258 A * | 4/1975 | Semola et al. ............. 81/121.1 |
| 4,006,660 A | 2/1977 | Yamamoto et al. | |
| 4,269,246 A | 5/1981 | Larson et al. | |
| 4,338,835 A | 7/1982 | Simons | |
| 4,459,074 A | 7/1984 | Capuano | |
| 4,970,922 A | 11/1990 | Krivec | |
| 5,019,080 A | 5/1991 | Hemer | |
| 5,258,016 A | 11/1993 | DiPoto et al. | |
| 5,277,531 A | 1/1994 | Krivec | |
| 5,279,190 A | 1/1994 | Goss et al. | |
| 5,378,101 A * | 1/1995 | Olson et al. ................. 411/405 |
| 5,435,680 A | 7/1995 | Schuster | |
| 5,461,952 A | 10/1995 | Goss | |
| 5,484,440 A | 1/1996 | Allard | |
| 5,794,715 A | 8/1998 | Norman | |
| 5,899,902 A | 5/1999 | Brown et al. | |
| 5,957,645 A | 9/1999 | Stacy | |
| 6,016,727 A | 1/2000 | Morgan | |
| 6,131,493 A | 10/2000 | Yamamoto et al. | |
| 6,135,892 A | 10/2000 | Donovan | |
| 6,155,761 A | 12/2000 | Donovan | |
| 6,158,310 A | 12/2000 | Goss et al. | |
| 6,199,455 B1 | 3/2001 | Wagner | |
| 6,269,716 B1 * | 8/2001 | Amis ........................ 81/121.1 |
| 6,328,515 B1 | 12/2001 | Donovan | |
| 6,343,531 B2 * | 2/2002 | Amis ........................ 81/121.1 |
| 6,367,358 B1 | 4/2002 | Stacy | |
| 6,477,923 B2 * | 11/2002 | Amis ........................ 81/121.1 |
| 6,520,991 B2 | 2/2003 | Huene | |
| 6,575,061 B2 | 6/2003 | Wagner | |
| 6,626,067 B1 | 9/2003 | Iwinski et al. | |

(Continued)

Primary Examiner—David B. Thomas
(74) Attorney, Agent, or Firm—McHale & Slavin PA

(57) ABSTRACT

A drive system for a surgical fastener is composed of a drive tool with a drive tip that mates closely with the recess formed in the head of a threaded fastener. The surgical fastener has a head with a quadrilobe fitting therein which closely mates with the quardilobe tip of the tool. The cooperating drive surfaces align the fastener and tool coaxially and produce four point contact equidistant about the circumference of said fastener significantly reducing angular excursions of the fastener during placement in the bone.

16 Claims, 4 Drawing Sheets

U.S. PATENT DOCUMENTS

| | | |
|---|---|---|
| 6,632,057 B1 | 10/2003 | Fauchet |
| 6,685,412 B2 | 2/2004 | Altarac et al. |
| 6,832,882 B2 | 12/2004 | Janisch, Jr. et al. |
| 6,843,153 B1 * | 1/2005 | Rawson-Harris ............. 81/120 |
| 6,945,142 B1 | 9/2005 | Chen |
| 6,951,158 B1 | 10/2005 | Edland |
| 6,997,085 B2 * | 2/2006 | Yamamoto ................. 81/121.1 |
| 7,051,624 B2 * | 5/2006 | Oleszek ....................... 81/120 |
| 2003/0077145 A1 * | 4/2003 | Altarac et al. .............. 411/402 |
| 2005/0268757 A1 * | 12/2005 | Walker ........................ 81/460 |

* cited by examiner

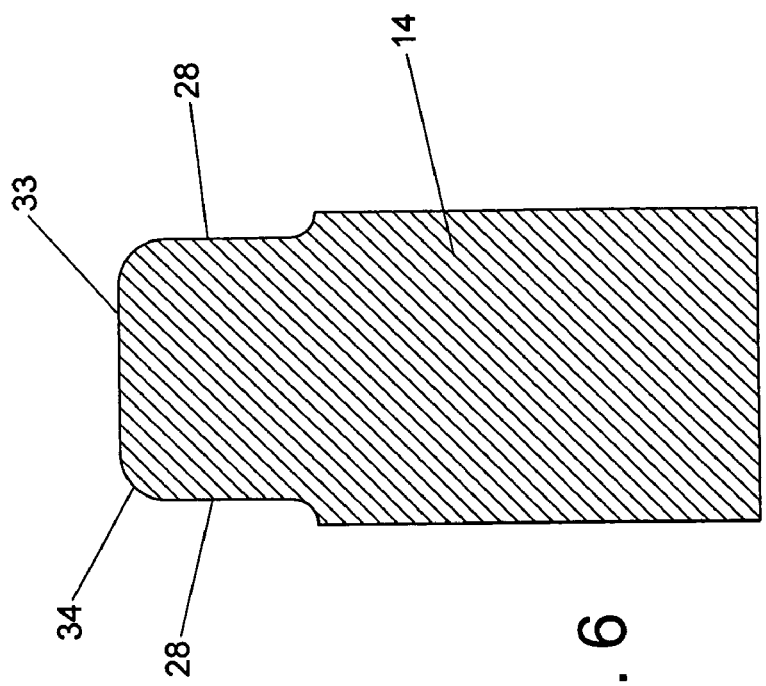
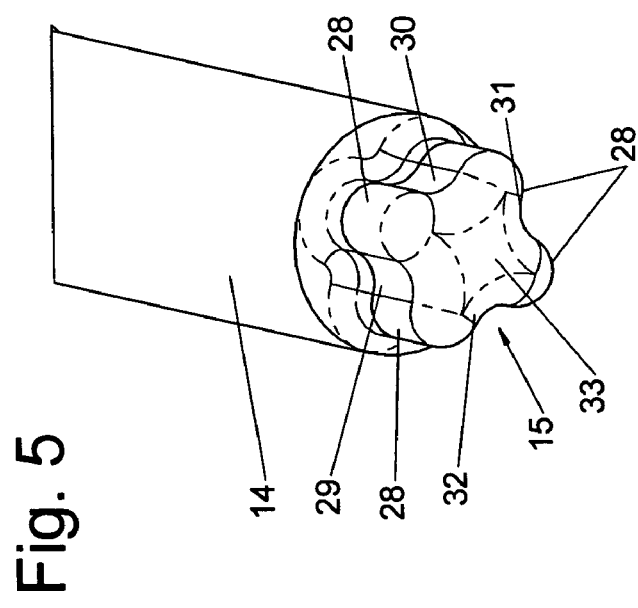

MEDICAL FASTENER AND TOOL

BACKGROUND OF THE INVENTION

1. Field of the Invention

The invention relates generally to threaded fasteners and fastener drives for the fasteners which make up a fastener drive system. The fastener drive system of this invention is especially useful in the medical arts which require that the fastener be oriented on the end of a drive tool in a coaxial position to eliminate any angular excursions between a prosthesis, the bone and the fastener.

2. Description of the Prior Art

There is a great deal of prior art teaching various forms of drive systems where one component is termed female and the other component is termed male with a cooperating recess and projection, respectively. Probably, the most common is the slotted screw head formed to accept the blade of a screw driver. Almost everyone knows that the tolerance between the slot and the blade is such that small side loads will turn the screw and disconnect the screw driver thereby creating a bore in the support that is larger than the thread diameter of the fastener. Further, as the screw tightens to form a fastening, the increasing torque causes the blade to spin out of the slot.

In surgery, the operating field is as small as possible and usually very confined which may restrict the approach of various tools to a less than optimum angle to the work area, producing side loads and reduced visibility, among other things, when placing a threaded fastener. The skeletal bone is made up of a hard outer casing surrounding a softer inner tissue so that maximum fastening forces are located in the outer thickness of the bone. Any wobble of the alignment of the fastener can lessen the purchase of the threaded fastener with the bone and significantly reduce the holding power of a threaded fastener.

U.S. Pat. No. 5,019,080 to Hermer teaches a drive system and fastener for surgical applications. The driver imparts rotational torque to the fastener and includes a tapered drive bit engagable with a tapered socket formed in the fastener. The bit and socket are formed with cooperating hexalobular surfaces. These surfaces form a triangular contact between the driver and the socket to prevent wobbling of the fastener when driven by the driver.

U.S. Pat. No. 5,279,190 to Goss et al is directed to an elliptical lobed drive system of general utility having a hexagonal configuration. One of the components, either the externally configured or the internally configured flutes and lobes, will be generated from ellipses of substantially equal dimension whereas the other component has flutes and lobes generated by ellipses of differing dimensions. The cooperating surfaces form a tapered interconnection.

The patent discusses the vector analysis of the forces generated during rotation of the system as composed of two components, a radial vector and a tangential vector. The tangential component is said to rotate or drive the fastener and is termed, "drive angle," which is defined by the angle made by a line tangent to the point of driver contact at the point of application and a radial line through the fastener or drive tool. The patent also states that generally speaking, the lower the drive angle, the more efficient the drive system. Further, when the drive angle exceeds a certain value, as for example 60 degrees, the torque loss is excessive and this situation should be avoided. Significantly, the more efficient the drive system, the less depth required for engagement of the lobes and flutes permitting smaller tools and screw heads on the fasteners.

By using the hexalobular construction in the drive system, these prior art devices rely on establishing a triangular contact array during operation of the system. In addition, the socket has a significant depth required by the triangular contact surfaces. However, the tapered form of the interconnection produces a tendency for the driving tool to spin-out of the recess under heavy torque forces.

What is needed in the art is a system to increase the contact surfaces and eliminate stress risers thereby reducing the force applied at each contact point, reducing the depth of the interconnection, shaping the walls of the interconnection to reduce spin-out and increasing the stability of the coaxial alignment between driver and fastener during rotation.

SUMMARY OF THE PRESENT INVENTION

Disclosed is a drive system for a surgical fastener or other screw fastener. The drive tool includes a drive tip that mates closely with the recess formed in the head of a threaded fastener. The surgical fastener has a head with a quadrilobe fitting therein which closely mates with the quardilobe tip of the tool. The cooperating drive surfaces align the fastener and tool coaxially and produce four point contact equidistant about the circumference of said fastener significantly reducing angular excursions of the fastener during placement in the bone.

Therefore, it is an objective of this invention to provide a drive system, including a cooperating fastener and drive tool, which assures coaxial alignment and secure connection between the tool and the fastener during engagement.

It is a further objective of this invention to provide increased surface contact between the fastener and the tool during rotation of the system.

It is another objective of this invention to provide a cooperating connection which resists angular excursions between the tool and fastener during rotation of the system by directing rotational forces in a plane perpendicular to the axis of the connection.

It is a still further objective of this invention to provide guiding and centering surfaces on the tool and the fastener for ease in joining the tool and the fastener as well as providing a transition area between the central axis and the contact surfaces.

It is yet another objective of this invention to provide cooperating quadrilobe fitting and tip on the fastener and tool with columnar lobes spaced equidistant about the circumference of the longitudinal axis of the fastener and the tool.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

SHORT DESCRIPTION OF THE DRAWINGS

FIG. 5 is a perspective of the tip of the tool;

FIG. 6 is a cross section of the tip of the tool of this invention;

DETAILED DESCRIPTION OF THE INVENTION

Figure 2:
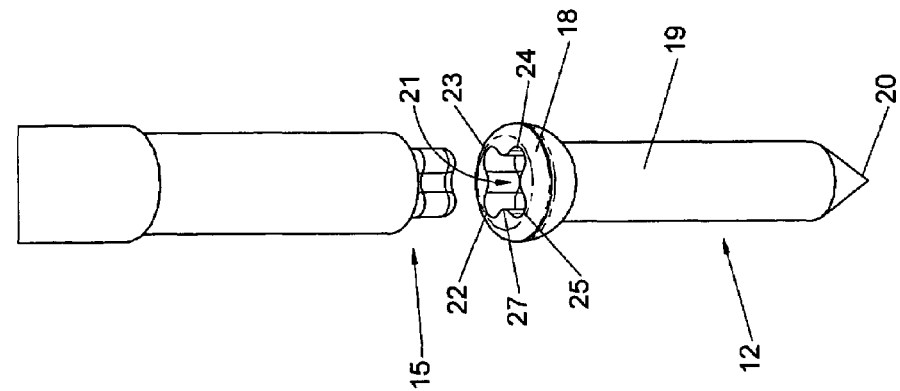
FIG. 2 is a perspective of the cooperating connection between the fastener and the tool of this invention.
Figure 1:
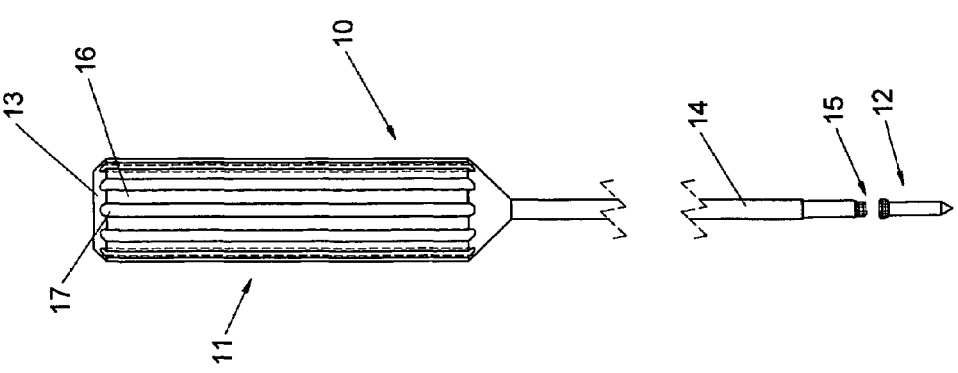
FIG. 1 is a side view of the tool and fastener of this invention.

The drive system 10, shown in FIG. 1, is illustrated as a hand tool 11 and a fastener 12. The hand tool has a grip 13 and a shaft 14 terminating in the cooperating tip 15. The grip 13 is constructed, for example, with alternating lands 16 and grooves 17 to improve the non-slip manipulation and rotation of the tool during driving of the fastener 12. However, the shaft 14 may have a chuck rather than a handle for use with power tools.

The fastener 12, in the preferred embodiment, is a surgical screw with a helical screw thread extending from the head 18 along the shank 19 to the leading end 20. There are numerous thread designs all of which are directed to increasing the purchase of the screw.

Further, there are self-tapping screws and screws used in pre-drilled holes. These latter types are directed to driving the screw without burring the bone-screw thread pattern. These screws reduce the wobble or angular excursions from the longitudinal axis produced by the side loads developed during rotation of a nonaligned tool and fastener. The fastener 12 may take the form of any of these different types of screws.

Figure 3:
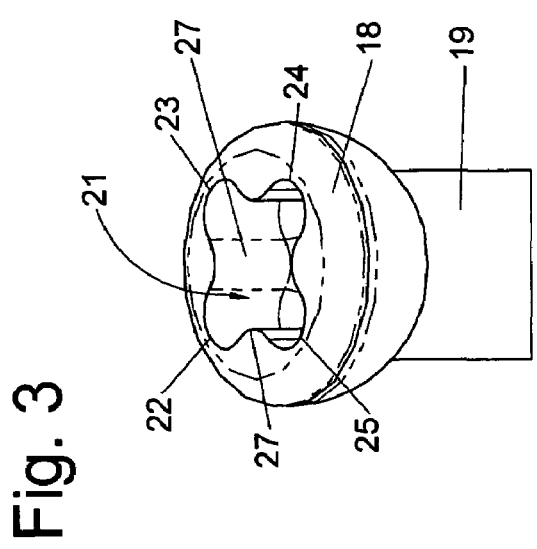
FIG. 3 is a perspective of the head of the fastener of this invention.

The head 18 of the fastener has a fitting or recess 21, shown in FIG. 3, which has dimensions slightly larger than the dimensions of the protrusion or tip of the driving tool. The periphery of the recess is a continuous curvilinear form having four distinct lobes 22, 23, 24, and 25 joined by a continuous sidewall 27. Each of the lobes is defined by an outer columnar circumference of approximately 180 degrees. The axes of the lobes are oriented parallel with the longitudinal axis of the fastener. The depth of the recess is sufficient to develop a telescoping fit with the tip of the driving tool. The depth of the recess is related to the quadrilobe form in that four contact surfaces require less depth than fewer contact surfaces. Also, the depth is such to maintain coaxial alignment during rotation of the driving tool.

Figure 4:
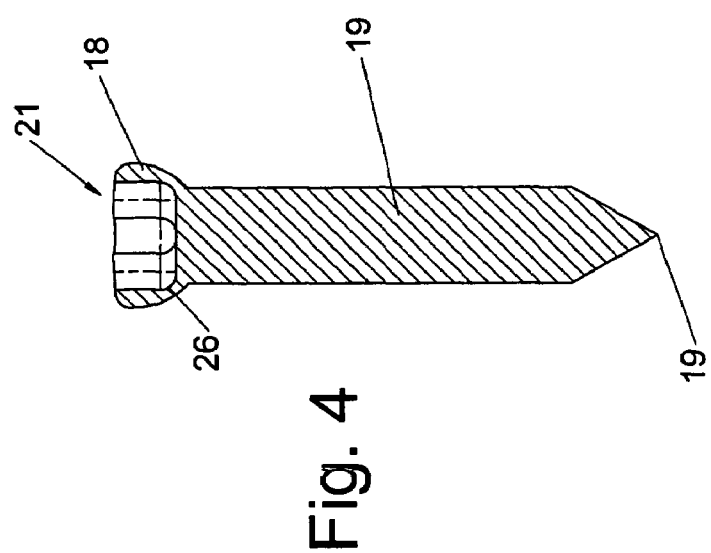
FIG. 4 is a cross section of the fastener of this invention.

As shown in FIG. 4, the bottom of the recess is flat. The transition portion 26 may be spherical in nature allowing the bottom ends of the lobes and the sidewall to smoothly change directions.

The cooperating tip 15 of the driving tool forms a protrusion of smaller diameter than the shaft 14. The tip is shaped as a quadrilobed projection with four lobes 28 spaced equidistant about the protrusion. The columnar shaped lobes each define an outer circumference of approximately 180 degrees and have an outer wall parallel with the longitudinal axis of the shaft. The lobes are joined by fillets 29, 30, 31 and 32 which are integral with the shaft 14 of the tool. The fillets are curvilinear to mirror the curve of the sidewall 27 of the recess in the fastener.

The end 33 of the protrusion is flat to contact the flat bottom of the recess in the fastener. The periphery of the end 33 matches the shape of the transition portion 26 of the recess. The rounded portion forms a guide 34 to facilitate the insertion of the tip 15 into the recess 21.

Once the tip end 33 is in contact with the bottom of the recess and the parallel walls of the quadrilobes of the protrusion are in contact with the parallel walls of the quadrilobes of the recess, the rotational forces at all four contact surfaces are directed normal to the axis of the interconnection.

Figure 7:
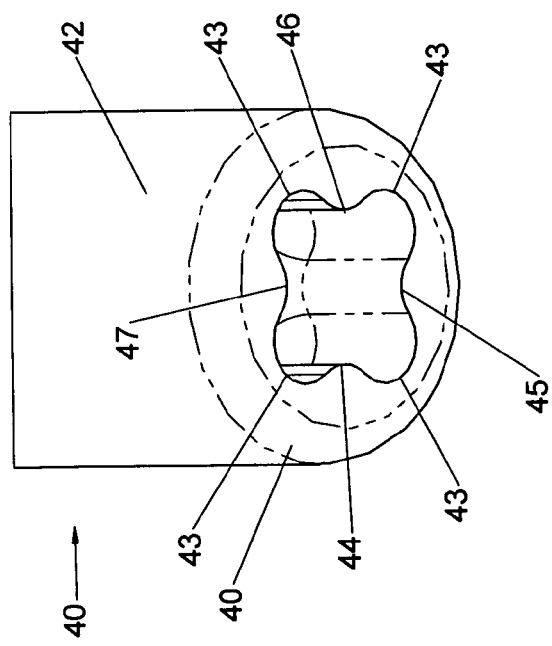
FIG. 7 is a perspective of another embodiment of the tip of the tool of this fastener.
Figure 8:
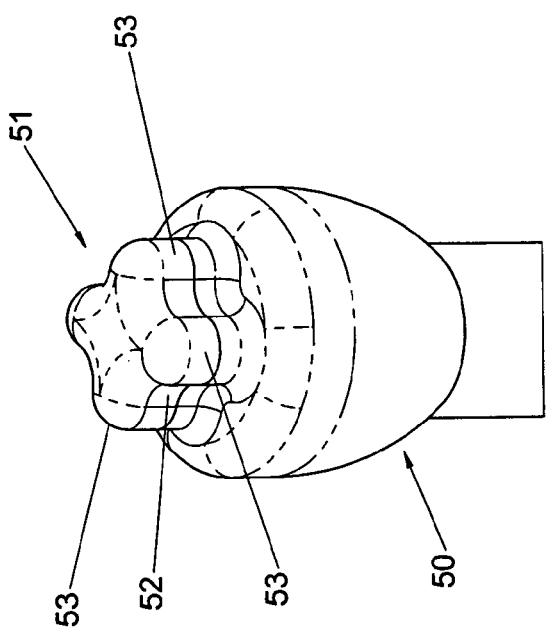
FIG. 8 is a perspective of another embodiment of the head of the fastener of this invention.

The combination of the screw fastener and tool may be provided in the reverse of the elements shown in FIGS. 1–6. As shown in FIGS. 7–8, the screw fastener is made with a turret head 51 and the tool has a coordinate recess 41. The cooperating tip 40 of the driving tool has a recess on the tip of the shaft 42. The recess 41 is shaped as a quadrilobed fitting with four lobes 43 spaced equidistant about the circumference, as described above. The lobes each define an outer circumference of approximately 90 degrees and have an outer wall parallel with the longitudinal axis of the shaft. The lobes are joined by fillets 44, 45, 46 and 47 which are integral with the shaft 42 of the tool. The fillets are curvilinear to mirror the curve of the sidewall 52 of the turret 51 on the fastener 50.

The turret 51 of the fastener 50 has, shown in FIG. 8, a protrusion of smaller diameter than the recess 41. The tip is shaped as a quadrilobed projection with four lobes 53 spaced equidistant about the protrusion. The height of the lobes matches closely the depth of the recess 41 and the sidewall is parallel with the longitudinal axis of the fastener.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A threaded fastener drive system, comprising:
   a screw fastener having a shank with a leading end, a head on the other end with a helical thread extending from said head to said leading end, a quadrilobe fitting on said head, said quadrilobe fitting forming a quadrilobe recess composed of four equally spaced columnar lobes, with the axis of each of said columnar lobes parallel with each other, each of said four columnar lobes connected to each other by a continuous sidewall forming a unitary curvilinear recess, a seat formed in said quadrilobe fitting, said seat having a substantially flat bottom of lesser diameter than said quadrilobe recess and a first continuous spherical transition wall between said bottom and said recess; and
   a drive tool having an elongated shaft having a first end and a second end, a quadrilobe drive tip connected to said first end of said shaft, said quadrilobe drive tip forming a quadrilobe protrusion, said protrusion composed of four equally spaced columnar lobes with the axis of each of said columnar lobes parallel with the longitudinal axis of said shaft, each of said four columnar lobes connected to each other by fillets forming an integral protrusion, said fillets being curvilinear whereby said quadrilobe protrusion closely engages said quadrilobe recess, and a first continuous spherical transition wall between said bottom and said recess;
   wherein said quadrilobe tip and said quadrilobe fitting each being of a size and shape to closely interlock whereby said shaft and said shank are coaxial during rotation of said helical thread.

2. A threaded fastener drive system of claim 1, further comprising said drive tool being a hand tool with a handle on said second end, said handle of a greater diameter than said shaft to increase rotational leverage at said quadrilobe tip.

3. A threaded fastener drive system of claim 1, further comprising a contact array between said quadrilobe tip and said quadrilobe fitting disposed at 90 degrees intervals about the circumference about said head of said fastener.

4. A threaded fastener drive system of claim 1, further comprising said quadrilobe tip forming said protrusion, said protrusion composed of four equally spaced columnar lobes, with the axis of each of said columnar lobes parallel with the longitudinal axis of said shaft, each of said four columnar lobes connected to each other by fillets forming an integral protrusion.

5. A threaded fastener drive system of claim 1, further comprising a guide formed in said quadrilobe tip, said guide terminating in a substantially planar surface normal to the axis of said shaft, said guide being of lesser diameter than said quadrilobe protrusion and a second continuous spherical transition wall between said planar surface and said tip.

6. A threaded fastener drive system of claim 5 further comprising a seat formed in said quadrilobe fitting, said seat having a substantially flat bottom of lesser diameter than said quadrilobe recess and a first continuous spherical transition wall between said bottom and said recess wherein said first and said second spherical wall closely engage each other.

7. A threaded fastener drive system comprising the combination of a drive tool having an elongated shaft having a first end and a second end, a protrusion of lesser diameter connected to said first end of said shaft, said protrusion having a quadrilobe drive tip, said quadrilobe tip composed of four columnar lobes equally spaced about the circumference of said quadrilobe tip, said columnar lobes integrally connected by a first continuous curvilinear sidewall, a guide formed in said quadrilobe tip, said guide terminating in a substantially planar surface normal to the axis of said shaft, said guide being of lesser diameter than said quadrilobe tip with a first continuous spherical transition wall between said planar surface and said quadrilobe tip and a surgical fastener having a shank with a leading end, a head on the other end with a helical thread extending from said head to said leading end, a recessed quadrilobe fitting on said head, said quadrilobe fitting composed of four equally spaced columnar lobes, each having an axis parallel with the longitudinal axis of said surgical fastener, each of said four columnar lobes connected to each other by a second continuous sidewall forming a unitary curvilinear recess, a seat formed in said curvilinear recess, said seat having a substantially flat bottom of lesser diameter than said curvilinear recess and a second continuous spherical transition wall between said bottom and said recess, the length of said quadrilobe tip being at least equal to the depth of said fitting whereby said first sidewall and said second sidewall contact each other in a four point array and said planar surface of said guide engages said seat during operation of the system producing rotational forces normal to said longitudinal axis.

8. A threaded fastener drive system of claim 7 further comprising the periphery of said quadrilobe tip including approximately 180 degrees of each of said four columnar lobes.

9. A threaded fastener drive system of claim 8 further comprising said periphery of said quadrilobe tip including said first continuous curvilinear sidewall extending tangentially between two adjacent lobes.

10. A threaded fastener drive system of claim 7 further comprising the periphery of said curvilinear recess including approximately 180 degrees of each of said four columnar lobes.

11. A threaded fastener drive system of claim 10 further comprising said periphery of said quadrilobe recess including said second continuous curvilinear sidewall extending tangentially between two adjacent lobes.

12. A threaded fastener drive system, comprising:

a drive tool having an elongated shaft having a first end and a second end, a quadrilobe drive tip connected to said first end of said shaft and forming a quadrilobe protrusion, a guide formed in said quadrilobe drive tip, said guide terminating in a substantially planar surface normal to the axis of said shaft, said guide being of lesser diameter than said quadrilobe protrusion and a second continuous spherical transition wall between said planar surface and said tip; and a screw fastener having a shank with a leading end, a head on the other end with a helical thread extending from said head to said leading end, a quadrilobe fitting on said head, said quadrilobe fitting forming a recess, said recess composed of four equally spaced columnar lobes with axis of each of said columnar lobes parallel with each other, each of said four columnar lobes connected to each other by a continuous sidewall forming a unitary curvilinear recess;

said quadrilobe drive tip and said quadrilobe fitting each being of a size and shape to closely interlock whereby said shaft and said shank are coaxial during rotation of said helical thread.

13. A threaded fastener drive system of claim 12 further comprising a seat formed in said quadrilobe fitting, said seat having a substantially flat bottom of lesser diameter than said quadrilobe recess and a first continuous spherical transition wall between said bottom and said recess wherein said first and said second spherical wall closely engage each other.

14. A threaded fastener drive system of claim 12, wherein said drive tool is a hand tool with a handle on said second end, said handle of a greater diameter than said shaft to increase rotational leverage at said quadrilobe tip.

15. A threaded fastener drive system of claim 12, further comprising a contact array between said quadrilobe tip and said quadrilobe fitting disposed at 90 degrees intervals about the circumference about said head of said fastener.

16. A threaded fastener drive system of claim 12, further comprising said quadrilobe tip forming said protrusion, said protrusion composed of four equally spaced columnar lobes, with the axis of each of said columnar lobes parallel with the longitudinal axis of said shaft, each of said four columnar lobes connected to each other by fillets forming an integral protrusion.

* * * * *